US007015022B2

(12) United States Patent
Laskin et al.

(10) Patent No.: US 7,015,022 B2
(45) Date of Patent: Mar. 21, 2006

(54) MAMMALIAN CATALASE-DEPENDENT OXIDATION PROCESSES AND METHODS FOR STIMULATING OXIDATIVE ACTIVITIES

(75) Inventors: Jeffrey D. Laskin, Piscataway, NJ (US); Anna Marie Vetrano, North Brunswick, NJ (US); Diane Heck, Rumson, NJ (US)

(73) Assignee: University of Medicine & Dentistry of New Jersey, New Brunswick, NJ (US)

( * ) Notice: Subject to any disclaimer, the term of this patent is extended or adjusted under 35 U.S.C. 154(b) by 366 days.

(21) Appl. No.: 10/165,841

(22) Filed: Jun. 7, 2002

(65) Prior Publication Data

US 2003/0228648 A1    Dec. 11, 2003

(51) Int. Cl.
*C12N 9/08* (2006.01)
(52) U.S. Cl. .................. 435/192; 435/27; 435/41; 435/156; 435/189; 8/101; 8/102
(58) Field of Classification Search ................ 435/192, 435/189, 27, 41, 156; 8/101, 102
See application file for complete search history.

(56) References Cited

U.S. PATENT DOCUMENTS

| | | | | |
|---|---|---|---|---|
| 4,306,025 | A | * | 12/1981 | Hasegawa et al. ........... 435/192 |
| 4,871,660 | A | * | 10/1989 | Gadow ........................ 435/7.72 |
| 5,135,860 | A | * | 8/1992 | Anton et al. ................. 435/136 |
| 5,610,025 | A | * | 3/1997 | White et al. ................... 435/25 |
| 5,728,684 | A | * | 3/1998 | Cheng et al. ................... 514/50 |
| 5,951,714 | A | * | 9/1999 | Hall et al. ....................... 8/102 |
| 6,080,573 | A | | 6/2000 | Convents et al. ............ 435/263 |
| 6,218,350 | B1 | | 4/2001 | Beggs et al. ................. 510/305 |
| 6,232,101 | B1 | | 5/2001 | Budolfsen et al. ............. 435/72 |
| 6,241,849 | B1 | | 6/2001 | Franks ........................... 162/5 |
| 6,245,269 | B1 | | 6/2001 | Viikari et al. ................ 264/109 |
| 6,248,134 | B1 | | 6/2001 | Damhus et al. ................. 8/111 |
| 6,251,845 | B1 | | 6/2001 | Herbots et al. .............. 510/320 |
| 6,288,128 | B1 | | 9/2001 | Yamamoto et al. ........... 514/739 |

FOREIGN PATENT DOCUMENTS

JP                06316874       * 11/1994

OTHER PUBLICATIONS

Cheng et al., "Photoinactivation of Catalase", Photochem. Photobiol. 1981 34:125-129.
Feierabend J. and Engel S., "Photoinactivation of Catalase in Vitro and in Leaves", Archives of Biochem. Biophys. 1986 251:567-576.
Kanski et al., "Ferulic acid antioxidant protection against hydroxyl and peroxyl radical oxidation in synaptosomal and neuronal cell culture systems in vitro:structure-activity studies", J. Nutr. Biochem. 2002 13:273-281.
Lu et al., "Inhibitory Effects of Orally Administered Green Tea, Black Tea, and Caffeine on Skin Carcinogenesis in Mice Previously Treated with Ultraviolet B Light (High-Risk Mice) :Relationship to Decreased Tissue Fat", Cancer Research 2001 61:5002-5009.
Mitchell R.L. and Anderson I.C., "Catalase Photoinactivation", Science 1965 150:74.
Zhou et al., "A Stable Nonfluorescent Derivative of Resorufin for the Fluorometric Determination of Trace Hydrogen Peroxide: Applications in Detecting the Activity of Phagocyte NADPH Oxidase and Other Oxidases", Anal. Biochem. 1997 253 (2) :162-168.
Zigman et al., "Structural and Functional Changes in Catalase Induced by Near-UV Radiation", Photochem. Photobiol. 1996 63:818-824.

\* cited by examiner

*Primary Examiner*—Leon B. Lankford, Jr.
(74) *Attorney, Agent, or Firm*—Licata & Tyrrell P.C.

(57) ABSTRACT

A catalase-dependent enzymatic oxidation process wherein a substrate to be oxidized is contacted with catalase in the absence of hydrogen peroxide is provided. Also provided are methods for using this process in a variety of biomedical, clinical and diagnostic applications as well as industrial processes. A method for stimulating the enzymatic oxidation process by treatment with ultraviolet light and uses for this method are also provided.

7 Claims, No Drawings

MAMMALIAN CATALASE-DEPENDENT OXIDATION PROCESSES AND METHODS FOR STIMULATING OXIDATIVE ACTIVITIES

INTRODUCTION

This invention was supported in part by funds from the U.S. government (NIH Grant No. ES 06897) and the U.S. government may therefore have certain rights in the invention.

FIELD OF THE INVENTION

The present invention relates to the newly identified ability of mammalian catalase to oxidize a broad range of substrates in the absence of hydrogen peroxide cofactor and the newly identified ability of exposure to ultraviolet light to accelerate the oxidation of substrates by catalase. The enzymatic processes of the present invention are useful in a variety of techniques and kits for use in biochemistry, diagnostics and molecular biology, as well as in industrial processes.

BACKGROUND OF THE INVENTION

Catalase has been one of the most intensely studied enzymes. This heme-containing redox protein is found in nearly all animal cells, plant cells and aerobic microorganisms. This enzyme is probably best known for its catalatic activity, breaking down potentially damaging hydrogen peroxide into oxygen and water. By preventing excessive build-up of hydrogen peroxide in cells, catalase permits the required cellular processes that produce hydrogen peroxide to take place. Catalase also possesses peroxidase activity, also known as peroxidatic activity, which allows catalase to oxidize certain low molecular weight alcohols in the presence of small amounts of the cofactor hydrogen peroxide.

A kit for assaying catalase activity via the substrate AMPLEX-RED™ is commercially available (Molecular Probes, Inc. 4849 Pitchford Avenue, Eugene, Oreg.). In this assay, catalase first reacts with hydrogen peroxide to produce water and oxygen. The AMPLEX-RED™ reagent is then added to react with any unreacted hydrogen peroxide in the presence of horse radish peroxidase to produce the highly fluorescent product resorufin (Zhou et al. Anal. Biochem. 1997 253(2):162–8). Thus, in this assay, as catalase activity increases, the signal from the resorufin decreases.

Modifications to catalase via acetylation or guanidation result in a loss in catalatic and peroxidatic activities. The catalatic activity of catalase has also been shown to be photoinactivated in vitro (Mitchell, R. L. and Anderson, I. C. Science 1965 150:74); Chen et al. Photochem. Photobiol. 1981 34:125–129; Feierabend, J. and Engel, S. Arch. Biochem. Biophys. 1986:251:567–576) and in cultured cells (Zigman et al. Photochem. Photobiol. 1996 63:818–824 and Giordani et al. Redox Report 1997 3:49–55) upon irradiation with high doses of ultraviolet or visible light.

It has now been found that mammalian catalase oxidizes a broad range of substrates in the absence of hydrogen peroxide. Further, it has now been found that exposure of mammalian catalase and substrates to low doses of ultraviolet light accelerates oxidation of the substrates.

SUMMARY OF THE INVENTION

An object of the present invention is to provide an enzymatic oxidation process wherein a selected substrate to be oxidized is contacted with mammalian catalase in the absence of hydrogen peroxide.

Another object of the present invention is to provide compositions, methods and kits for using this mammalian catalase-dependent oxidation process in applications including, but not limited to, stain bleaching and anti dye-transfer in detergents, polymerization of lignin, in-situ depolymerization of lignin in Kraft pulp, bleaching of denim dyed garments and other printed or dyed fabric or yarn, polymerization of phenolic substances in juices and beverages, antimicrobial treatment of microorganisms and/or viruses, hair bleaching and detoxification of phenolic and other hydrogen based electron donating pollutants.

Another object of the present invention is to provide an enzyme substrate system comprising mammalian catalase and a selected substrate for the oxidative activity of mammalian catalase wherein mammalian catalase oxidizes the selected substrate in the absence of hydrogen peroxide. In a preferred embodiment, the selected substrate is oxidized to a fluorescent product so that the enzyme substrate system can be used in chemifluorescence techniques. Laccases can be substituted for mammalian catalase in this embodiment of use in chemifluorescence techniques when AMPLEX-RED™ is the substrate.

Another object of the present invention is to provide a method for accelerating oxidation of substrates by mammalian catalase by exposure of the substrate and mammalian catalase to ultraviolet light. In this method, a selected substrate for the oxidative activity of mammalian catalase is added to mammalian catalase and then treated with low doses of ultraviolet light to accelerate oxidation of the selected substrate.

Yet another object of the present invention is to provide screening assays to identify compounds that modulate activity of mammalian catalase and/or inhibit acceleration of mammalian catalase activity by ultraviolet light. Screening assays of the present invention are also useful in identifying agents that are activated by mammalian catalase.

DETAILED DESCRIPTION OF THE INVENTION

Current technologies typically utilize peroxidases and hydrogen peroxide or microbial oxidative enzyme such as laccase to carry out oxidation reactions. It has now been found that the mammalian enzyme catalase can be used in oxidation reactions without the need for addition of hydrogen peroxide as a cofactor.

A binding site has now been identified that provides mammalian catalase with the ability to oxidize a broad range of substrates. This oxidative activity appears to be independent of the known catalatic and peroxidatic functions of mammalian catalase. The broad specificity of this newly identified oxidase activity of mammalian catalase render oxidation processes described herein useful in a wide variety of techniques in biochemistry, basic and clinical pharmacology, diagnostics and molecular biology, as well as in industrial processes.

For example, in one embodiment, the catalase-dependent oxidation process is useful in chemifluorescence techniques wherein mammalian catalase oxidizes a selected substrate to a fluorescent product. Chemifluorescence has become the standard non-isotopic detection method for DNA, RNA or proteins using a membrane transfer technology such as Western blotting or Northern blotting. It is based upon the affinity binding of an enzyme-conjugated probe to a target molecule. Under appropriate conditions, the enzyme continuously converts a non-fluorescent substrate to an intensely fluorescent product, continually increasing the signal of the target molecule. The enzymatic activity of alkaline phosphatase and an appropriate substrate is currently used for this important technique. However, as demonstrated herein, mammalian catalase can also be used to catalyze the oxidation of a non-fluorescent substrate such as the dye 10-acetyl-3,7-dihydroxyphenoxazine (molecular formula $C_{14}H_{11}NO_4$; molecular weight 257.25; AMPLEX-RED™, Molecular Probes) to a highly fluorescent product, in this case resorufin ($^3$H-phenoxazin-3-one, 7-hydroxy, sodium salt; molecular formula $C_{12}H_6NNaO_3$; molecular weight 235.17) without the addition of hydrogen peroxide.

Experiments were performed to determine the time and temperature dependence of the oxidation of AMPLEX-RED™ to resorufin by mammalian catalase in the absence of hydrogen peroxide. Resorufin concentrations, which were measured via fluorescence (540 nm excitation wavelength, 595 nm emission wavelength), increased fairly linearly over the time range of 0 to 20 minutes in assays performed at 0° C. and at room temperature. However, resorufin concentrations were much higher in assays performed at room temperature. Elevation of the assay temperature above room temperature to 45° C. resulted in a slight reduction in resorufin production, while an increase to 50° C. resulted in a greater reduction in resorufin production. Increasing the temperature to 55° C. or greater eliminated almost all resorufin production. Thus, oxidation of substrates by mammalian catalase in the absence of hydrogen peroxide appears to be optimal at room temperature.

The effects of other substrates on oxidation of AMPLEX-RED™ to resorufin by catalase were also examined. Addition of 1,2,3-trihydroxybenzene(pyrogallol),2,2'-azino-bis (3-ethylbenz-thiazoline-6-sulfonic acid)(ABTS), 4-dimethylaminoantipyrene (aminopyrene), 2',7'-dichlorodihydrofluorescein diacetate (DCFH-DA), 3,3'-dimethoxybenzidine (DMB), 1,8-diaminonapthalene (DAN), 4-hydroxy-3-methoxycinnamic acid (HMCA), 1,2-dihydroxybenzene (catechol, DHB), and 3,3'-diaminobenzidine (DAB), at concentrations ranging from 0.005 mM to 0.1 mm or greater resulted in inhibition of the oxidation of AMPLEX-RED™ to resorufin by catalase. These compounds were also substrates for the oxidase reaction. Further studies of the kinetics of this enzyme inhibition showed pyrogallol, ABTS, DCFH-DA, DMB, DAN, HMCA, DHB and DAB to be competitive inhibitors while aminopyrene was a noncompetitive inhibitor. By "noncompetitive inhibitor" it is meant a compound which inhibits by binding to enzyme sites that participate in both substrate binding and catalysis. As shown by these experiments, there are a large number of substrates and inhibitors of mammalian catalase oxidase activity. Further, as shown, there are at least two mechanisms by which inhibitors of the reaction can function. This understanding is useful in the design of new substrates and inhibitors of mammalian catalase oxidase activity.

Prior art assays with AMPLEX-RED™ require addition of peroxidase and hydrogen peroxide to measure catalase activity. For catalase detection using AMPLEX-RED™, catalase unknowns are first reacted with hydrogen peroxide. AMPLEX-RED™ is then added to react with any unreacted hydrogen peroxide and form the fluorescent product resorufin. Thus, catalase activity is taught in the prior art to be measurable by comparing the amount of resorufin formed in the absence of catalase with the lower amount of fluorescence in samples containing catalase. More specifically, catalase activity is taught to be inversely proportional to the amount of resorufin product formed after 30 minutes. Thus, the prior art AMPLEX-RED™ assay for catalase monitors decreasing fluorescence which is oftentimes less sensitive. A less sensitive prior art assay for catalase activity requires measuring decreasing absorbance with the substrate scopoletin. Accordingly, use of catalase to oxidize a substrate such as AMPLEX-RED™ in accordance with the present invention provides a simpler, more sensitive enzyme substrate system which is highly effective in detecting low levels of DNA, RNA and protein on membrane blots. DCFH-DA can also be used in place of AMPLEX-RED™. This enzyme substrate system can be used in any technique involving immunoblotting, DNA and RNA blotting and is particularly useful in applications where there is a need for prolonged signal amplification. Further, as will be understood by those of skill in the art upon reading this disclosure, other color forming substrates well known in the art for use in Western and Northern blotting as well as immunohistochemistry with peroxidases, can also be used in accordance with the present invention to measure activity of mammalian catalase. Examples of the broad range of substrates for mammalian catalase that are active in the absence of hydrogen peroxide include, but are not limited to, those compounds depicted herein in Table 1.

TABLE 1

Exemplary Substrates Oxidized by Mammalian Catalase

| Inhibitor | | Structure |
|---|---|---|
| 2',7'-dichlorodihydrofluorescein diacetate | DCFH | 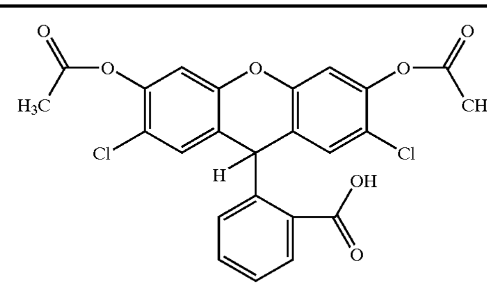 |

TABLE 1-continued

Exemplary Substrates Oxidized by Mammalian Catalase

| Inhibitor | | Structure |
|---|---|---|
| 3,3'-dimethoxybenzidine | DMB | 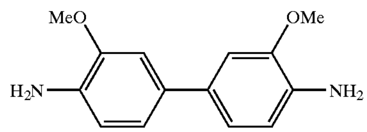 |
| 1,8-diaminonaphthalene | DAN | 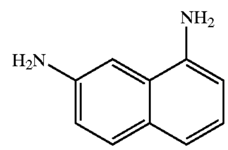 |
| 4-hydroxy-3-methoxycinnamic acid (ferulic acid) | HMCA | 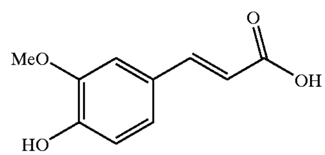 |
| 1,2-dihydroxybenzene (catechol) | DHB | 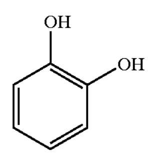 |
| (−)-epigallocatechin-3-gallate | EGCG | 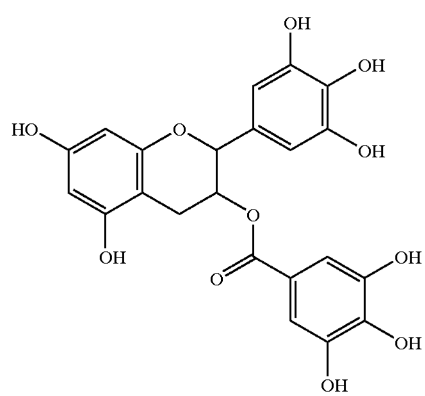 |
| 5-amino-2,3-dihydro-1,4-phthalazine-dione (luminol) | LUM | 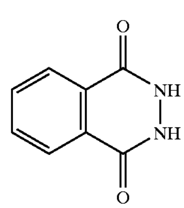 |
| 2,2'-azino-bis [3-ethyl benzthiazoline-6-sulfonic acid] | ABTS | 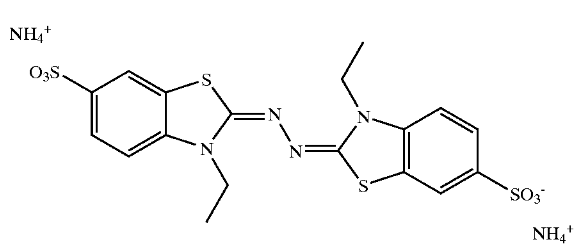 |

TABLE 1-continued

Exemplary Substrates Oxidized by Mammalian Catalase

| Inhibitor | | Structure |
|---|---|---|
| 3,3'-diaminobenzidine | DAB | (structure of 3,3'-diaminobenzidine) |
| 1,2,3-trihydroxybenzene (pyrogallol) | PYR | (structure of pyrogallol) |
| 3-amino-1,2,4-triazole | ATZ | (structure of 3-amino-1,2,4-triazole) |
| sodium azide | AZ | $NaN_3$ |
| 4-dimethylaminoantipyrine | DMAP | (structure of 4-dimethylaminoantipyrine) |
| Benzidine | BENZ | (structure of benzidine) |
| 4,4'-diamino-3,3'dimethyl-biphenyl (o-tolidine) | TOL | (structure of o-tolidine) |
| cyclophosphamide | CPP | (structure of cyclophosphamide) |
| NDH 4174 | | (structure of NDH 4174) |

TABLE 1-continued

Exemplary Substrates Oxidized by Mammalian Catalase

| Inhibitor | Structure |
|---|---|
| NDH 4143 | 3-(furan-2-yl)-4-{[(E,2E)-3-(5-nitrofuran-2-yl)prop-2-en-1-ylidene]amino}-4H-1,2,4-triazole-5-thiol |
| NDH 4152 | 3-(furan-2-yl)-5-(methylsulfanyl)-4-{[(E,2E)-3-(5-nitrofuran-2-yl)prop-2-en-1-ylidene]amino}-4H-1,2,4-triazole |
| NDH 4138 | 4-{[(E,2E)-3-(5-nitrofuran-2-yl)prop-2-en-1-ylidene]amino}-3-(thiophen-2-yl)-4H-1,2,4-triazole-5-thiol |
| NDH 4126 | 3-(methylsulfanyl)-4-{[(E,2E)-3-(2-nitrophenyl)prop-2-en-1-ylidene]amino}-5-(thiophen-2-yl)-4H-1,2,4-triazole |
| NDH 4009 | 4-{[(E,2E)-3-(2-nitrophenyl)prop-2-en-1-ylidene]amino}-5-(thiophen-2-yl)-4H-1,2,4-triazole-3-thiol |
| NDH 4054 | 3-methyl-4-{[(E,2E)-3-phenylprop-2-en-1-ylidene]amino}-4H-1,2,4-triazole-5-thiol |
| NDH 4110 | 4-{[(E,2E)-3-(2-nitrophenyl)prop-2-en-1-ylidene]amino}-4H-1,2,4-triazole |
| NDH 4119 | 3-(methylsulfanyl)-4-{[(E,2E)-3-(2-nitrophenyl)prop-2-en-1-ylidene]amino}-4H-1,2,4-triazole |

TABLE 1-continued
Exemplary Substrates Oxidized by Mammalian Catalase
| Inhibitor | Structure |
|---|---|
| NDH 4097 | 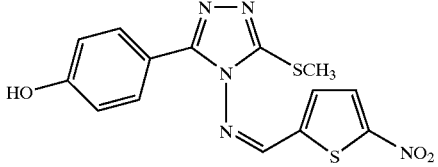 |
| NDH 4091 | 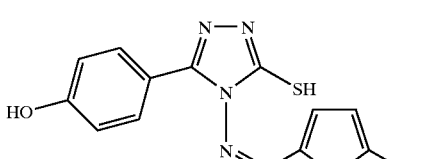 |
| NDH 4139 | 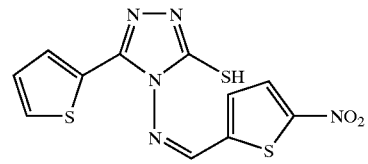 |
| NDH 4144 | 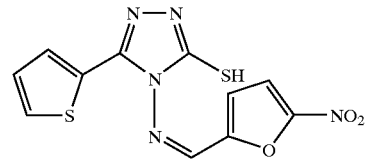 |
| NDH 4169 | 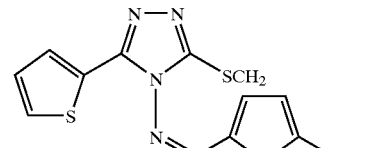 |
| NDH 4146 | 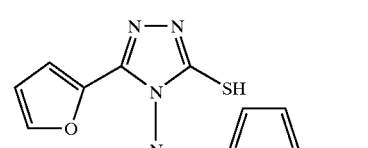 |
| NDH 4158 | 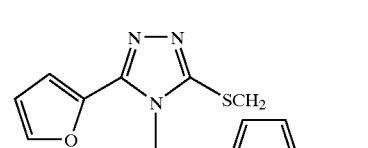 |
| NDH 4165 | 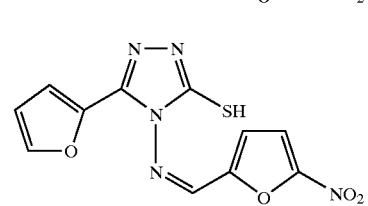 |

TABLE 1-continued

Exemplary Substrates Oxidized by Mammalian Catalase

| Inhibitor | Structure |
|---|---|
| NDH 4150 | (furan-triazole-SCH2-thiophene-NO2 structure with N=N linker) |

An additional exemplary substrate useful in the present invention is diaminobenzidine, a common peroxidase substrate used in these techniques. Diaminobenzidine forms a brown precipitate which allows for visualization of a protein bound antibody in a tissue section. Other examples of substrates include, but are not limited to, luminol and compounds related thereto. Luminol is a competitive inhibitor of the AMPLEX-RED™ reaction. Luminol and compounds related thereto are important in chemiluminescence procedures.

The enzymatic generation of fluorescent or colored dyes has great value in the biomedical research field as well as for clinical diagnostics. In general, assays in these areas comprise detection of a molecule via an alkaline phosphatase conjugate, a beta galactosidase conjugate or a horse radish peroxidase conjugate and an appropriate substrate. However, a catalase conjugate and a selected substrate for the oxidative activity of catalase can be routinely substituted in accordance with the teachings provided herein into any of these assays without any requirement for addition of a cofactor. Further, the assay of the present invention may be advantageous over alkaline phosphatase or galactosidase under certain circumstances where there may be high backgrounds or other prohibitive reaction conditions. In addition, the assay of the present invention provides an additional means for detection when there is a need for detection of multiple signals (see roche-applied-science.com).

Laccases can also be used in chemifluorescence techniques with the substrates AMPLEX-RED™ and DCFH-DA. Laccases are multi-copper oxidases that can catalyze the oxidation of a range of substrates with the concomitant reduction of oxygen. It has now been found that laccases can also be used with AMPLEX-RED™ in similar fashion to mammalian catalase as an enzyme substrate system with no requirement for the cofactor hydrogen peroxide.

The present invention also provides kits for assaying mammalian catalase oxidation of a selected substrate. Examples of components of these kits include, but are not limited to, the selected substrate, preferably AMPLEX RED or DCFH-DA at 200 or 5 micromolar final concentration, respectively, phosphate buffer, preferably 50 mM at pH 7.4, and a mammalian catalase, preferably bovine liver catalase. In a preferred embodiment, the mammalian catalase is directly conjugated to specific antibody (direct immunodetection) or directly conjugated to secondary antibody (indirect immunodetection).

The assays and kits of the present invention are useful in immunoblotting techniques. For example, for a Western Blot analysis, a test sample is first run on a 10% SDS-polyacrylamide gel. It is then transferred via electroblotting onto nitrocellulose paper. The blot is then incubated with a primary antibody directed against the antigen of interest. This primary antibody is either directly conjugated to catalase or the blot is reacted with a secondary antibody conjugated to catalase (e.g, if the primary antibody is a rabbit antibody, the secondary antibody can be goat-anti-rabbit conjugated to catalase or if the primary antibody is a mouse monoclonal antibody, the secondary antibody can be goat anti-mouse antibody conjugated to catalase). The blot is then incubated in phosphate buffer containing a selected substrate, preferably AMPLEX-RED™. Formation of a fluorescent product, preferably resorufin, can then be detected with a fluorescence imaging system.

Given the broad specificity of the oxidase activity of mammalian catalase, industrial processes utilizing this newly identified oxidase function can also be developed.

For example, the oxidase activity of catalase renders it useful in industrial, commercial, cosmetic and detergent compositions and as a bleaching enzyme. Use of laccases and peroxidases as detergent compositions and in bleaching methods is described in U.S. Pat. No. 6,251,845, and U.S. Pat. No. 6,218,350, respectively, which are herein incorporated by reference in their entirety. U.S. Pat. No. 6,080,573 also describes an enzymatic oxidation process for enzymatic stain bleaching comprising reacting a substance to be oxidized with (a) an enzyme exhibiting peroxidase activity and a source of hydrogen peroxide or an enzyme exhibiting oxidase activity on phenolic compounds and (b) a compound which enhances the oxidation activity of the enzyme. Enzymes exhibiting oxidase activity on compounds taught to be useful in U.S. Pat. No. 6,080,573 are catechol oxidase (note, in essence, catalase is a catechol oxidase although it is a different protein than the one described as catechol oxidase), laccase and bilirubin oxidase. However, similar detergent compositions and bleaching methods can now be developed which comprise catalase.

The oxidase activity of mammalian catalase also renders it useful in processes for removal of excess dyes and/or inks. For example, use of enzymes exhibiting peroxidase activity or laccase activity in a process for removal of excess dyes from newly manufactured printed or dyed fabrics and yarn is described in U.S. Pat. No. 6,248,134, which is herein incorporated by reference in its entirety. In this process, the newly manufactured printed or dyed fabric or yarn is treated with a rinse liquor comprising a peroxidase or laccase enzyme, an oxidation agent, and at least one mediator selected from the group consisting of aliphatic, cyclo-aliphatic, heterocyclic or aromatic compounds containing an N—OH moiety, preferably 1-hydroxybenzotriazole. Based upon the teachings provided herein, one of skill in the art could routinely substitute catalase in the rinse liquor instead of laccase or another peroxidase and use this method without requiring addition of hydrogen peroxide.

Catalase can also be substituted for a laccase enzyme in methods for deinking and decolorizing of printed papers such as described in U.S. Pat. No. 6,241,849, the teachings of which are incorporated herein by reference in their entirety. In this method, the printed paper is first pulped to obtain a pulp slurry. The ink is then dislodged with one or more selected enzymes known in the art to dislodge ink particles contained in the pulp. Exemplary ink dislodging enzymes include, but are not limited to, amylase, cellulase, hemicellulase, lipase, pectin methylesterase, protease, xylanase, or combinations thereof. The dye contained in the pulp slurry is then decolorized with catalase in the presence of oxygen. The released ink is then separated from the pulp slurry and the decolorized pulp is recovered. Similar amounts of catalase as taught for laccase in U.S. Pat. No. 6,241,849 can be used in this method.

Catalase can also serve as the oxidase instead of laccases or catechol oxidases in methods for promoting gelling or increasing viscosity of an aqueous medium containing gellable polymeric materials with phenolic hydroxy substituents. Methods for promoting gelling or increasing viscosity of an aqueous medium containing gellable polymeric materials with phenolic hydroxy substituents via other oxidases such as laccases and catechol oxidases are taught in U.S. Pat. No. 6,232,101, the teachings of which are herein incorporated by reference in their entirety. In a preferred embodiment, the gellable polymeric materials are phenolic polysaccharides such as arabinoxylans and pectins. The amount of catalase to be added to promote gelling or increase viscosity is similar to that taught for laccase in U.S. Pat. No. 6,232,101. Gelled products or products with increased viscosity produced via oxidation with catalase are useful in a wide range of applications including, but not limited to, food and feed areas, pharmaceutical and agricultural areas, and personal care/personal hygiene areas.

Enzymatic oxidation via catalase can also be used to polymerize solubilized wood materials in the production of fiber boards. Methods for enzymatic oxidation via other oxidase such as laccases, catechol oxidases, tyrosinases and bilirubin oxidases are described in U.S. Pat. No. 6,245,269, the teachings of which are herein incorporated by reference in their entirety. Based upon the teachings provided herein, catalase can now be routinely substituted into the methods of U.S. Pat. No. 6,245,269 to polymerize solubilized wood materials for production of fiber boards. Similar concentrations of catalase to those taught for laccase in U.S. Pat. No. 6,245,269 can be used.

Catalase, like laccase, can also be used for antimicrobial treatment of microorganisms and/or viruses as taught in U.S. Pat. No. 6,288,128, the teachings of which are herein incorporated by reference in their entirety. In this method, the microorganisms and/or viruses are treated with an effective amount of catalase and one or more enhancers as set forth in U.S. Pat. No. 6,288,128, in the presence of oxygen.

Mammalian catalase enzyme activity is also believed to be important in cellular biochemistry. For example, oxidation by mammalian catalase may be involved in the detoxification of toxins, the activation of drugs, and in the metabolism of endogenous substrates. Accordingly, mammalian catalase assays of the present invention may also be used in drug screening to identify compounds which inhibit activity of this enzyme. In these screening assays, oxidation of a selected substrate by mammalian catalase is measured in the presence and absence of a test compound. A decrease in oxidation of the selected substrate in the presence of the test compound is indicative of the test compound being an inhibitor of mammalian catalase activity. Compounds identified as inhibitors of mammalian catalase activity may be useful as chemopreventative agents and in the prevention of the breakdown of drugs by oxidation reaction.

The present invention also provides screening assays to identify agents, and in particular pharmacological agents, activated by oxidation by mammalian catalase. For example, it is known that dietary constituents can inhibit the development of cancer and neurologic damage. Several of the substrates for mammalian catalase disclosed in Table 1 are dietary constituents that have been associated with the beneficial effects. Ferulic acid, listed in Table 1 as a substrate for mammalian catalase, is an antioxidant which is believed to provide protection against neuronal damage (Kanski et al. J. Nutr. Biochem. 2002 13:273–281) and epigallocatechin, also listed in Table 1 as a substrate, is an active ingredient in green tea associated with prevention of cancer (Lu et al. Cancer Res. 2001 61:5002–5009). Analogs of these compounds can be tested in a mammalian catalase assay of the present invention, such as the AMPLEX-RED™ fluorescence assay, to identify new pharmacological agents oxidated by mammalian catalase to drugs with similar beneficial activities. Additional pharmacological agents such as prodrugs activated to drug by oxidation by mammalian catalase can be identified in similar fashion by contacting the prodrug with the enzyme and measuring the amount of drug produced.

The above descriptions of various applications for the catalase-dependent oxidative enzyme process of the present invention are merely exemplary and in no way limit the invention to these particular applications. Other various applications which rely upon the newly identified oxidative activity of catalase will be understood by those of skill in the art upon reading this disclosure and are meant to be encompassed within the present invention.

The present invention also relates to methods for accelerating the oxidation of substrates by catalase by exposure to ultraviolet light. For purposes of the present invention, by "accelerate" or "accelerating" it is meant that the rate at which catalase oxidizes a substrate is increased when exposed to ultraviolet light as compared the rate of oxidation of the substrate by catalase in the absence of ultraviolet light. In this method, a substrate is added to mammalian catalase and the mixture is then treated with low doses of ultraviolet light to accelerate oxidation of the substrate. In a preferred embodiment of this method, the low dose of ultraviolet radiation ranges between 2.5 and 25 $mJ/cm^2$ at a wavelength of UVB light that is between 290 and 320 nm. Preferred substrates for use in the present invention include those exemplified herein which are oxidated by mammalian catalase in the absence of hydrogen peroxide. For example, the substrate DCFH-DA was added to a reaction mixture containing catalase in sodium phosphate buffer. The samples were then exposed to increasing doses of ultraviolet light (UVB, 290–320 nm). Oxidation of DCFH-DA is observed in the absence of UVB light as measured by the increase in fluorescence (catalase+DCFH-DA). However, UVB light was found to cause a marked enhancement of DCFH-DA oxidation reaction (catalase+DCFH-DA+UVB light). This is believed to be due, at least in part, to UVB light induced formation of reactive oxygen intermediates by catalase that are known to accelerate oxidation.

Accelerating the oxidation of substrates by catalase by exposure to ultraviolet light results in production of a much greater signal in chemifluorescent techniques. Accordingly, the method of the present invention is useful in increasing the sensitivity of chemifluorescent techniques including, but not limited to, Western blotting and Northern blotting. The method of the present invention is also useful in decreasing the time required to develop fluorescence in chemifluorescent techniques.

In addition, mammalian catalase assays of the present invention comprising a UVB acceleration step can be used to identify new compounds which inhibit this acceleration. It is believed that these compounds may be useful in preventing damage to the skin and eyes following overexposure to ultraviolet light. In these assays, oxidation of a selected substrate by catalase exposed to ultraviolet light is measured in the presence and absence of a test compound. A decrease in oxidation of the substrate in the presence of the test compound as compared to oxidation of the substrate in the absence of the test compound is indicative of the test compound inhibiting damage of tissue relating to exposure to ultraviolet light. Thus, the present invention also provides screening assays for new drugs which protect against tissue damage from ultraviolet light.

The following nonlimiting examples are provided to further illustrate the present invention.

EXAMPLES

Example 1

Catalase-Dependent Oxidation of AMPLEX-RED™

AMPLEX-RED™ (10-acetyl-3,7-dihydroxyphenoxazine) is a substrate for mammalian catalase. In the presence of this enzyme, AMPLEX-RED™ is oxidized to the fluorescent product resorufin. This occurs with purified catalases obtained from a variety of sources including enzyme from mouse and bovine liver. The reaction also occurs with twice crystallized bovine liver catalase. For these experiments, AMPLEX-RED™ and resorufin were purchased from Molecular Probes (Eugene, Oreg.). Catalases were purchased from Sigma Chemical Co., St. Louis, Mo. Reactions were carried out in buffer consisting of 50 mM phosphate buffer, pH 7.4 and 1.0 mg/ml of the catalase at room temperature (22° C.) in a reaction volume of 0.1 ml. The reaction is initiated by the addition of appropriate concentrations of AMPLEX-RED™. Standard reaction mixtures contain 20 nmoles of the substrate. Detection of the fluorescent product resorufin was measured using an HTS 7000 Plus Bio Assay Reader (Perkin Elmer, Beaconsfield, Buckinghamsire, UK) using a 540 nm excitation filter and a 595 nm emission filter.

Temperature dependency of the reaction was tested by incubating the reaction mixture on ice or at room temperature for a minimum of 5 minutes prior to the addition of substrate. Fluorescence was measured at 5 minute intervals keeping one plate on ice or at room temperature between measurements. The reaction rate was much slower in the plate kept on ice. After 25 minutes, the plate which had been on ice was warmed to room temperature and fluorescence was measured in 5 minute intervals for another 20 minutes. This treatment caused a marked increase in the reaction rate.

Catalase (1 mg/ml) in reaction buffer was also incubated at different temperatures ranging from 22° C. to 60° C. for 5 minutes. AMPLEX RED was then added and the reaction rate measured on the fluorescence microplate reader. The data demonstrate that heat can inactivate the enzyme. Enzyme activity was almost completely inactivated at 55° C. and 60° C. and partly inactivated at 50° C. only a small inhibition was observed at 45° C.

pH dependency of the enzymatic reaction was also examined. In these experiments, the catalase oxidation reaction was performed as described above except that buffers ranging in pH from 4.0–10.0 were substituted for the standard reaction buffer of 50 mM phosphate buffer, pH 7.4. Fluorescence was measured after 10 minutes. Data from these experiments demonstrate that the oxidation reaction of catalase was pH dependent, with a pH ranging from 7–8 being preferred and a pH of 7.4 being more preferred.

Example 2

Competition with AMPLEX-RED™

Various compounds compete with AMPLEX-RED™ for binding to the active site of the catalase oxidase activity and are substrates for the enzyme. Catalase (1 mg/ml) in reaction buffer was incubated with AMPLEX-RED™ in the presence and absence of different substrate. The oxidation of AMPLEX-RED™ was then measured and the enzyme kinetics of the oxidation reaction measured. AMPLEX-RED™ oxidation was found to be linear with respect to catalase protein concentration (0.1–1 mg/ml) and time for at least 60 minutes. Using increasing concentrations of AMPLEX-RED™, oxidation of the substrate was found to be saturable and reversible. Using Lineweaver-Burke enzyme kinetic analysis, the Michaelis constant (Km) for the AMPLEX-RED™ was found to be $2.44 \times 10^{-4}$ M and the Vmax $4.74 \times 10^{-5}$ M/second. Various substrates were found to be inhibitors of the oxidation of AMPLEX-RED™ oxidation reaction (see Table 1). This includes many compounds that have been used in peroxidase reactions (e.g., 3,3'-diaminobenzidine). 3-amino-1,2,4-triazole, a known catalase inhibitor, inhibits the AMPLEX-RED™ catalase oxidase activity. A number of newly synthesized related triazole derivatives have also been found to be inhibitors of the catalase oxidase activity. Kinetic analysis demonstrated that the substrates could be divided into two classes, competitive inhibitors of the AMPLEX-RED™ oxidase reaction and non-competitive inhibitors of the AMPLEX-RED™ oxidase reaction. All compounds tested were found to be competitive inhibitors of the AMPLEX-RED™ catalase oxidation reaction except 4-dimethylaminoantipyrine. The Ki's for inhibition of each substrate were calculated and found to range from $3.16 \times 10^{-5}$ for 2', 7'-dichlorodihydrofluorescein to $1.68 \times 10^{-3}$ for 1,2,3-trihydroxybenzene (pyrogallol). For the triazole compounds, the Ki's range from $7.41 \times 10^{-5}$ to $7.12 \times 10^{-2}$. Based on the kinetic analysis, there is a specific active site on catalase for the oxidase reaction.

Many of the inhibitors in Table 1 are substrates for the catalase oxidase activity and form colored or fluorescent products. Alternatively, the substrate is colored and the oxidation reaction causes a decrease in absorbance that can be measured spectrophotometrically.

The oxidation of multiple substrates depicted in Table 1 with time was measured using an HTS 7000 Plus Bio Assay Reader using standard catalase reaction mixes (0.5 mg/ml catalase in 50 mM phosphate buffer, pH 7.4). Pyrogallol oxidation (1 mM) was measured by the increase in absorbance at 430 nm. Oxidation of ABTS (1 mM) was measured as the decrease in absorbance at 430 nm. Oxidation of catechol (1 mM) was measured as the increase in absorbance at 420 nm. Oxidation of DCFH (5 $\mu$M) by catalase was measured as the increase in fluorescence over time with a 485 nm excitation filter and a 520 nm emission filter.

Example 3

Accelerating Catalase Oxidation with UV Light

The oxidation of substrates by catalase can be accelerated by exposure to ultraviolet light. In these experiments, DCFH-DA (5 µM) was added to distilled water containing catalase (1 mg/ml) or bovine serum albumin (BSA, 1 mg/ml) as an inactive control, or distilled water as a control. Samples were then exposed to increasing doses of ultraviolet light (UVB, 290–320 nm) emitted from a bank of two FS20 UVB light bulbs (Sylvania). Relatively low levels of oxidation of DCFH-DA were observed in the absence of UVB light as measured by the increase in fluorescence (catalase+ DCFH-DA). However, UVB light was found cause a marked enhancement of DCFH-DA oxidation reaction (catalase+ DCFH-DA+UVB light). No activity was observed in reaction mixes containing $H_2O$ or BSA either in the presence or absence of UVB light. These data demonstrate that ultraviolet light can accelerate the oxidation of substrates by catalase.

What is claimed is:

1. An enzymatic oxidation process wherein a selected substrate to be oxidized is contacted with mammalian catalase in the absence of hydrogen peroxide.

2. The enzymatic oxidation process of claim 1 wherein the selected substrate is oxidized by mammalian catalase to a fluorescent product.

3. The enzymatic oxidation process of claim 1 wherein the selected substrate is oxidized by mammalian catalase to a chemiluminescent product.

4. A screening assay for compounds that inhibit mammalian catalase comprising measuring oxidation of a selected substrate for hydrogen peroxide independent mammalian catalase activity by mammalian catalase in the presence and absence of a test compound, wherein a decrease in oxidation of the selected substrate in the presence of the test compound is indicative of the test compound inhibiting hydrogen peroxide independent mammalian catalase activity.

5. A screening assay to identity pharmacological agents activated by oxidation comprising contacting the pharmacological agent with mammalian catalase and measuring for activation of the pharmacological agent in the absence of hydrogen peroxide.

6. The screening assay of claim 5 wherein the pharmacological agent is a prodrug and activation is measured by amount of drug produced.

7. A method for accelerating oxidation of a selected substrate for hydrogen peroxide independent mammalian catalase activity by mammalian catalase comprising exposing a mixture containing the selected substrate and mammalian catalase to a low dose of ultraviolet B radiation ranging between 2.5 and 25 $mJ/cm^2$ at a wavelength between 290 and 320 nanometers.

* * * * *